United States Patent [19]

Sommers et al.

[11] 4,384,792
[45] May 24, 1983

[54] PROCESS AND APPARATUS FOR THE COMBUSTIONLESS MEASUREMENT AND/OR CONTROL OF THE AMOUNT OF HEAT FED TO GAS CONSUMPTION DEVICES

[75] Inventors: Hans Sommers, Essen; Wilhelm Korsmeier; Friedrich Vissel, both of Recklinghausen, all of Fed. Rep. of Germany

[73] Assignee: Ruhrgas Aktiengesellschaft, Essen, Fed. Rep. of Germany

[21] Appl. No.: 169,702

[22] Filed: Jul. 17, 1980

[30] Foreign Application Priority Data

Jul. 17, 1979 [DE] Fed. Rep. of Germany ....... 2928739

[51] Int. Cl.³ ............................................. G01N 25/30
[52] U.S. Cl. ....................................................... 374/36
[58] Field of Search .......... 73/54, 55, 190 R, 190 CV; 364/509, 558; 374/36

[56] References Cited

U.S. PATENT DOCUMENTS

| 2,674,118 | 4/1954 | Westmoreland | 73/55 |
| 3,610,026 | 10/1971 | Topham | 73/55 |
| 3,783,684 | 1/1974 | De Livois | 73/190 |

FOREIGN PATENT DOCUMENTS

| 657696 | 9/1951 | United Kingdom | 73/51 |
| 1118645 | 7/1968 | United Kingdom | 73/190 |

Primary Examiner—Herbert Goldstein
Attorney, Agent, or Firm—Martin A. Farber

[57] ABSTRACT

A process and apparatus for the combustion-less measurement and/or regulation of the feeding of quantities of heat to gas combustion devices, particularly natural-gas combustion devices. A fuel gas or a partial stream of the fuel gas is fed through a fuel gas line containing at least one flow resistor which produces a laminar flow and a pressure drop. The gas volume flow and/or the pressure drop over at least one flow resistor is measured by a volume flow metering device and a difference pressure regulator, respectively, the pressure drops and/or volume flows which are not measured being maintained constant. A device compensates for the influence of temperature on the system is compensated. The measured value(s) in accordance with the formula described in the specification $$f(H) = \frac{1}{a + b \cdot n^c \cdot p^d}$$

is a measure of the heat content of the flowing gas and results in a signal which serves for measurement and/or regulation.

34 Claims, 9 Drawing Figures

PROCESS AND APPARATUS FOR THE COMBUSTIONLESS MEASUREMENT AND/OR CONTROL OF THE AMOUNT OF HEAT FED TO GAS CONSUMPTION DEVICES

The present invention relates to a method for the combustion-less measurement and/or control of the amount of heat fed to gas consumption devices, particularly natural-gas consumptin devices, as well as apparatuses for the carrying out of the different variations of the process.

For measurement of the gross calorific value or other properties of combustible gases such as the net calorific value or Wobbe Index it was heretofore customary to burn a partial stream of the combustible gas in a suitable apparatus (calorimeter) with open flame or on a catalyst and to measure the heat thereby produced. The measurement value supplied by these apparatus can be used to indicate the aforementioned properties of the gas or as a signal for control processes, for instance in order to maintain the gross calorific value or the Wobbe Index of a stream of gas constant by the feeding of other gases or to suitably change the quantitative flow of gas.

The necessity of burning a measured partial stream of the gas in order to measure the gross calorific value or the Wobbe Index requires, as known from experience, frequent maintenance of the apparatus since the flame can change due to deposits of combustion residues or because combustion catalysts gradually decline in effectiveness. The required accuracy of measurements which serve, for instance, for billing purposes can only be obtained if these apparatus are operated under well-defined, controlled conditions—preferably in an air-conditioned chamber—which also means a high expense.

Methods are also known for continuously analyzing a stream of gas without combustion, for instance by absorption of different components of the gas in suitable solvents, by gas chromatography, or by measuring the absorption of infrared radiation. From the continuously determined percentages of different gases in the stream of gas it is then possible, for instance by means of an electronic computer, continuously to display or use as a control pulse the gross calorific value, the net calorific value or the Wobbe Index of the gas being examined. However, these methods require a large expenditure for measurement and control devices.

Methods for measuring amounts of heat are already being used today in practice for numerous purposes. Recently the interest in and need for such measurements have increased considerably for various reasons. In industrial heating processes it is frequently necessary to feed a well-defined amount of heat per unit of time to a furnace in order to obtain optimum results. In other cases it is desired to optimize the consumption of fuel, i.e. to feed only the amount of heat actually required even if supplying of a larger amount of heat does not adversely affect the process or product. For billing purposes recently billing on the basis of the amount of heat supplied has also been preferred to billing on a volume basis.

An extensive need has arisen, for the above cases of use for measurements of the amount of heat which have been indicated by way of example above, due to the distribution of combustion gases and particularly natural gases of different origin whose composition and properties differ to a greater or lesser extent from each other. Since processes and apparatus have been developed and proven themselves for the use of such gases, despite these differences in gas consumption devices, without having to effect changes in the consumption devices when changing the quality of the gas, the measurement of the quantity of heat is gaining increasing importance both in the industrial use of gas and for billing purposes.

The known methods are, however, in many cases not applicable for the new purposes due to technical reasons or reasons of cost.

The object of the present invention is to effect the measurement of combustible-gas properties such as gross calorific value, net calorific value or Wobbe Index without combustion of gas and in a simpler manner than with the previously known combustion-less methods.

Anothr object achieved by the invention consists in continuing to properly feed a predetermined amount of heat to the following gas consumption device or devices by varying the volumetric flow of gas upon a change in the quality of the gas.

The invention which is described below is based on the surprising discovery that the Wobbe Index of natural gases of different origin and composition and of other combustible gases is, with a high degree of precision, a function of the viscosity of these gases.

The upper standard Wobbe Index $W_{o,n}$ and the upper operating Wobbe Index $W_o$ are, as is known, defined by the expressions $$W_{o,n} = \frac{H_{o,n}}{\sqrt{d_v}} \tag{1}$$

$$W_o = \frac{H_o}{\sqrt{d_v}} \cdot \sqrt{\frac{p_o \cdot T}{p \cdot T_o}} = \frac{H_o}{\sqrt{\frac{p}{p_{L,n}}}} \tag{2}$$

in which $$H_{o,n} = \frac{p_o \cdot T}{P \cdot T_o},$$

the stand gross calorific value (formerly the gross calorific value)
$H_o$ is the operating gross calorific value
$d_v$ is the specific gravity of the gas, referred to air=1
$p$ is the gas operating density, $$\rho = \rho_n \cdot \frac{p \cdot T_o}{p_o \cdot T}$$

$\rho_{L,n}$ is the standard density of the air.

In similar manner there are defined the lower standard Wobbe Index $W_{u,n}$ and the lower operating Wobbe Index $W_u$ which refer to the standard net calorific value $H_{u,n}$ (formerly net calorific value and the operating net calorific value $H_u$.

From equations (1) and (2) it can be seen that it should be possible to utilize the newly found relationship between viscosity and Wobbe Index for the determination of net calorific or gross calorific value if the density of the gas is known or measured.

From these findings there has been developed, with the use of known methods for the determination of viscosity and density of gases, a manner of technical action which forms the subject matter of this invention and is set forth in the claims.

The invention is based on the general relationship $$f(H) = f(n, \rho) \quad (3)$$

from which the empirically found general formula $$f(H) = a + b \cdot n^c \cdot \rho^d \quad (4)$$

has been developed as a first approximation, referring to given operating conditions (p, T=constant).

The letters used in these formulas have the following meanings:
f (H)=function of the heat of reaction of the gas, for instance $H_o, nH_u$, $W_{o,n}$, $W_u$ in MJ/M$^3$
a,b,c,d=constants which have different numerical values depending on the meaning of f (H)-gross calorific or net calorific value, upper or lower Wobbe Index.
n=dynamic gas viscosity in Ns/m$^2$
$\rho$=operating gas density in kg/m$^3$.

The validity and the dispersion range of formula (4) were verified for numerous cases with different meanings of f (H), for instance for $H_{o,n}$, $H_u$, $W_{o,n}$, $W_u$. This will be explained further, later on, on the basis of examples.

Formula (4) shows that the values of f (H) are characterized in particular by the variables n and $\rho$. The determination of these variables can be effected in principle by any method. The methods known at the present time in part require considerable expense.

There will be considered here, in accordance with the invention, only methods of determination which are based on the physical laws or relationships set forth below.

For the pressure drop $\Delta p$ between the inlet and outlet side of a pipe which is traversed by a fluid there applies, in the case of laminar flow (Re$\leq$2300) in accordance with the Hagen-Poiseulle law, the relationship $$\Delta p_1 = \frac{32 \cdot l \cdot u_1 \cdot n}{d_h^2} \quad (5)$$

the symbols of which have the following meaning:
Re=Reynolds number
$\Delta p_1$=pressure difference upon laminar flow in N/m$^2$
$u_1$=average gas velocity in m/s
l=pipe length in meters
$d_h$=hydraulic pipe diameter in m
n=dynamic gas viscosity in Ns/m$^2$
With constant geometrical conditions, we have $u_1 = V_1/F$, in which $V_1$ is the volumetric flow and F the cross section of the pipe.

By means of equation (5) there is obtained herefrom:

$$n \sim \frac{\Delta p_1}{V_1} \quad (6)$$

For the velocity $u_t$ of gas flowing with turbulent flow through a nozzle there follows, from the principle of the conservation of energy $$u_t = k \cdot g \cdot e \cdot \sqrt{\frac{2\Delta p_t}{\rho}} \quad (7)$$

In this formula the symbols not used up to now have the following meaning:
k=nozzle constant
g=discharge coefficient
e=expansion coefficient
$\Delta p_t$=pressure difference upon turbulent flow in N/m$^2$ From formula (7) there is obtained for constant geometric conditions, the relationship $$\rho \sim \frac{\Delta P_t}{V_t^2} \quad (8)$$

The (measurable) pressure differences $\Delta p_1$ and $\Delta p_t$ are accordingly a measure of the gas viscosity n and the gas density $\rho$. The above-indicated relationships or physical laws are utilized with the verification of the present invention with a combination of equations (4), (6) and (8).

$$f(H) = a + b \cdot \left(\frac{\Delta p_1}{V_1}\right)^c \cdot \left(\frac{\Delta p_t}{V_t^2}\right)^d$$

In this connection, physical properties in the arrangements determine in part the constants a, b, c, d of formula (9). The output signal of these arrangements therefore more or less precisely approximates formula (4) and thus provides a measure for f (H).

For the carrying out of the method of the invention it is necessary, in each case, to determine the dynamic gas viscosity, which is a measure of the standard Wobbe Index of the gas. This measurement is effected in known manner by means of a flow resistance which produces a laminar gas flow and is referred to in the following as laminar resistance.

In accordance with equation (6) there are three possibilities for this:
1. The pressure drop over the laminar resistance is maintained constant and the quantity flowing through is measured.
2. The pressure drop over the laminar resistance is measured and the quantity flowing through is maintained constant.
3. The pressure drop over the laminar resistance and the quantity flowing through are measured simultaneously.

If the net calorific or gross calorific value is to be obtained, it is furthermore necessary to determine the density of the gas. This measurement is effected in known manner by means of a flow resistance which produces a turbulent gas flow and is referred to hereinbelow as a turbulence resistance.

In accordance with equation (8) there exist in this connection fundamentally the same three possibilities as indicated above for the laminar resistance.

By combination of laminar and turbulence resistances the pressure drops and volume flows which are measured and/or controlled, the output variables of the measurement arrangements can, depending upon the purpose of use, be used directly or after conversion, as control and/or display signals.

In the following, the corresponding physical relationships for a few measurement arrangements selected by way of example will be described, without taking into consideration the influence of temperature or total pressure. In this way, an unnecessary complicating of the formulas which would impair overall understanding is avoided. The possibilities for compensating for temperature and for absolute pressure effect on the results will be described after the description of the apparatus.

The required physical values of the individual gas components (for $\rho_n, n, H_{o,n}, H_{u,n}, W_{o,n}, W_{u,n}$) and a few gas mixtures are taken from leading standards and manuals [1 to 4]. For the calculation of the physical values of further mixtures, the formulas set forth in Reference [4] are taken as basis. In Table 1 there are indicated compositions and physical values by way of example for 4 qualities of gas of the natural gas family taken from Reference [5]. In the following, natural gas H (see Table 1) serves as reference gas (subscript b), i.e. the behavior of the gases flowing through an arrangement is considered as compared with the behavior of natural gas H. In this way other dimensional constants are dispensed with.

In order to make the method of the invention clear, there are described in detail below, with reference to FIGS. 1 to 7, various illustrative apparatus and their manners of operation. The individual apparatus parts are shown diagrammatically in the figures. Identical apparatus parts are provided with identical numbers in all figures.

If only the Wobbe Index of a gas is to be measured, it is sufficient to use a measurement device which consists of a volume-flow measuring or metering device and a laminar resistance and to maintain either the volume flow or the pressure difference constant in known manner while the other variable is measured. Such a measuring arrangement is shown diagrammatically by way of example in FIG. 1.

Figure 1:
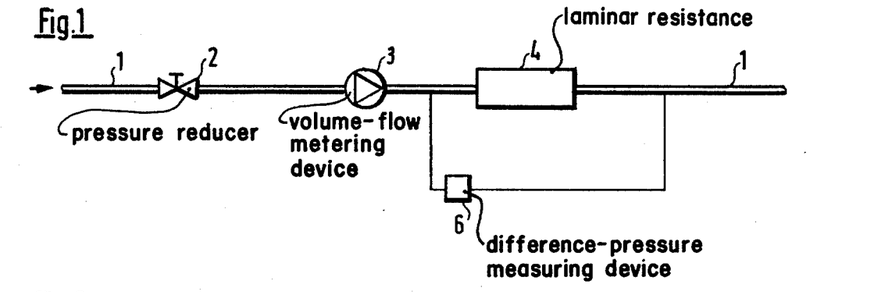
FIG. 1 is a schematic illustration of one measuring arrangement of the present invention.

The gas flows in the direction indicated by the arrow through the gas line 1 which branches off from a main gas line (not shown) and in which a pressure reducer 2 is arranged in front of the measurement arrangement which consists of volume-flow metering device 3, laminar resistance 4 and difference-pressure measuring device 6. The volume-flow metering device 3 assures constant volume-flow of the gas. The measured difference pressure which, at constant temperature or with suitable temperature compensation, is a measure of the normal Wobbe Index of the gas flowing at the time, can be transmitted in known manner to an indicating or control apparatus, either directly or after pneumatic amplification or conversion into electric pulses. After flowing through the measuring arrangement the gas can be fed back to the main gas line or to a gas consumption device. The last-mentioned method is advisable, for instance, in the case of industrial gas-consuming devices in which the quantities fed in this way are negligible as compared with the demand.

The signal of the difference-pressure measurement device 6 is linearly dependent on the standard Wobbe Index. Its value decreases with an increase in the standard Wobbe Index.

If the signal of the measuring device is to reproduce the operating Wobbe Index then temperature and absolute-pressure (barometer-level) compensation are required.

Possibilities for this are indicated after the description of the devices.

For the measurement arrangement in accordance with FIG. 1 we have:

$$\frac{\Delta p_1}{\Delta p_{1,b}} = \frac{n}{n_b} \quad (10)$$

$$n = \frac{n_b}{\Delta p_{1,b}} \cdot \Delta p_1 \quad (11)$$

Since $n_b$ and $\Delta p_{1,b}$ are known and constant, the output signal $\Delta p_1$ is directly a measure of the viscosity n of the unknown gas, which in its turn, for the reasons indicated above, constitutes a sufficiently exact measurement for Wobbe Indices. The influence of the gas density is not taken into consideration here, i.e. the constant d of formula (4) is equal to zero. Arrangements by which the gross calorific or net calorific value are to be determined must in addition contain at least one turbulence resistance so that the density of the gas can be included in the output signal, and the expression $\rho^d$ in formulas (4) and (12) assume a value other than 1.

By inserting formula (11) into formula (4) there is accordingly obtained for the relationship of $\Delta p_1$ and $W_{u,n}$ $$W_{u,n} = a + b \cdot \left(\frac{n_b}{\Delta p_{1,b}} \cdot \Delta p_1\right)^c \cdot 1 \quad (12)$$

$$W_{u,n} = a + b \cdot \left(\frac{n_b}{\Delta p_{1,b}}\right)^c \cdot \Delta p_1^c \quad (13)$$

The constants a, b and c of formula (13) have, for instance, the following values for the arrangement in accordance with FIG. 1 for the determination of $W_{u,n}$ in MJ/m³:

a = 199.1
b = −74211
c = 0.542

Figure 2:
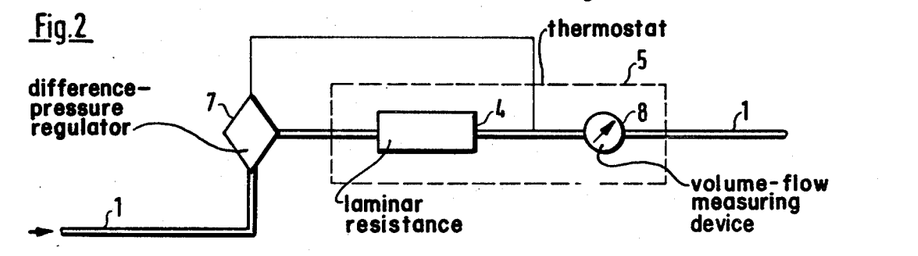
FIG. 2 is a schematic illustration of another measurement device of the present invention.

Another measurement device which also supplies a signal for the standard Wobbe Index is shown in FIG. 2. Here the gas is conducted through an analogous gas line 1 into the measurement arrangement which consists of a laminar resistance 4, the pressure drop of which is maintained constant by means of the difference-pressure regulator 7, and of a volume-flow measurement device 8. The temperatures of the laminar resistance 4 and of the volume-flow measuring device 8 are jointly held constant by a thermostat 5. Instead of this it is possible to obtain the necessary compensation of the influence of the temperature on the system solely by thermostatizing a part of the laminar resistance (4).

In this arrangement the indication or the signal given off by the volume-flow measurement device 8 is a measure of the standard Wobbe Index and, in the event of an increasing standard Wobbe Index, the quantity of gas flowing increases, i.e. the signal changes in the same direction and/or with the same sign as the standard Wobbe Index.

This arrangement can be so modified, without changing its manner of action, that the volume-flow measuring device 8 is arranged, as seen in the direction of flow, in front of the laminar resistance 4, whose difference pressure is maintained constant.

For a reproduction of the operating Wobbe Index, temperature and absolute-pressure compensation is required, as indicated with respect to FIG. 1.

For the measurement arrangement in accordance with FIG. 2 we have:

$$\frac{V_1}{V_{1,b}} = \frac{n_b}{n} \quad (14)$$

$$n = n_b \cdot V_{1,b} \cdot \frac{1}{V_1} \quad (15)$$

Similar to formula (13), by inserting formula (15) into formula (4) we obtain for the relationship of $V_1$ and $W_{o,n}$:

$$W_{o,n} = a + b \cdot (n_b \cdot V_{1,b})^c \cdot \left(\frac{1}{V_1}\right)^c \quad (16)$$

The constants a, b and c of formula (16) have, for instance, for the arrangement in accordance with FIG. 2 for the determination of $W_{o,n}$ in $MJ/m^3$ the values
a = 113.8
b = −7.216 . 10$^8$
c = 1.425

Figures 3, 4:
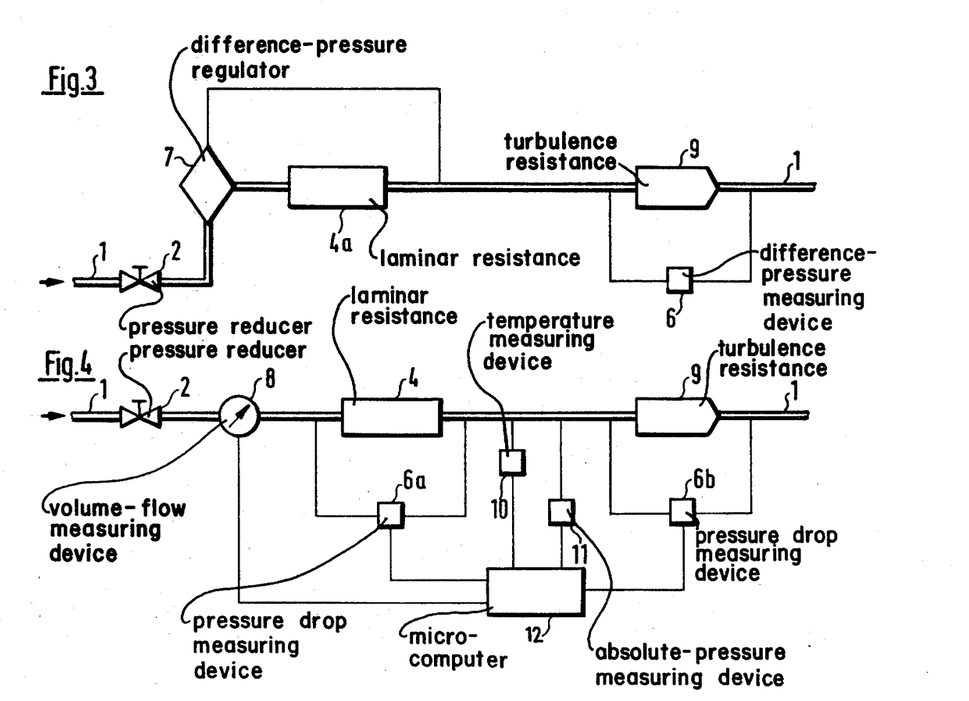
FIG. 3 is a schematic illustration of a direct measuring system of the present invention.
FIG. 4 is a schematic illustration of a measurement arrangement having a volume-flow device in accordance with the present invention.

With the apparatus shown in FIG. 3, the operating heating value or the operating combustion value of a gas is measured directly, since in this arrangement a turbulence resistance 9 is arranged in the stream of gas in addition to the laminar resistance 4a. In this apparatus the pressure drop over the laminar resistance 4a is maintained constant by means of the difference-pressure regulator 7 while the pressure drop over the turbulence resistance 9 is measured. A suitable temperature compensation sees to it that the temperature variation 4 the difference pressure measured at the measuring device 6 is equal to that of the operating net calorific value. If a signal is desired for the standard net calorific value or gross calorific value, a corresponding temperature and absolute-pressure compensation is required.

The measurement arrangement shown in FIG. 3 is excellently suited, due to its simple embodiment, inter alia, for the conversion of the volume measurement of a gas meter into an energy quantity measurement and due to the exact reproduction of the dependence of the operating net calorific value on the gas density, for direct measurements under increased pressure.

FIG. 4 shows a measurement arrangement in which a volume-flow measuring device 8, for instance a gas meter, a laminar resistance 4 and a turbulence resistance 9 as well as a temperature measuring device 10 and absolute-pressure measuring device 11 are arranged in the gas line 1 behind a pressure reducer 2. The pressure drop is measured with suitable measuring devices 6a, 6b over both flow resistances. The values measured at the instruments 8, 6a, 6b, 10 and 11 are transmitted in known manner, for instance after conversion into electrical pulses, to the microcomputer 12 which transmits the measurement values to display or recording devices and/or transmits pulses to control or regulating members in the main gas line.

By the use of the microcomputer 12 it is not only possible with this arrangement to indicate the directly measured values (gas volume flow, difference pressures, temperature and absolute pressure of the gas) but also derived values can be indicated or transmitted to recording instruments or given off as control pulses, for instance Wobbe Indices, net calorific value, gross calorific value as well as gas density and viscosity, and this both for operating and for standard conditions.

This type of measurement arrangement is particularly suitable when a plurality of gas consumption devices which must be individually controlled are arranged behind the measurement arrangement. The arrangement is also suitable for installation in measurement stations of high-pressure long distance gas transmission (pipe) lines in which the (heat) quantity flow is continuously recorded.

Figure 5:
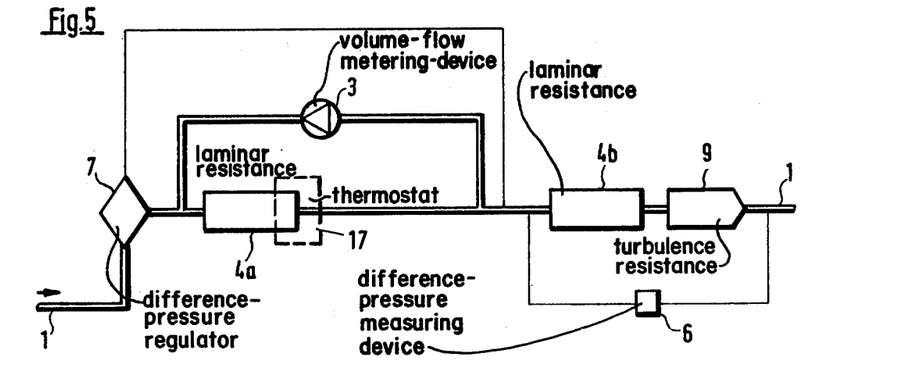
FIG. 5 is a schematic illustration of another measuring arrangement in accordance with the present invention differing from that shown in FIG. 3.

The measurement arrangement shown in FIG. 5 differs from the one described in FIG. 3 by the fact that a second laminar resistance 4b is arranged in the gas path and by the fact that by means of the volume-flow metering device 3, a given quantity of gas is branched off from the gas line behind the laminar resistance 4a and fed back to the gas line again in front of the laminar resistance 4a, i.e. a given amount of gas is in this way recycled. Behind the laminar resistance 4a there are connected in the gas path the laminar resistance 4b and a turbulence resistance 9. The pressure drop over the two last-mentioned flow resistances is measured. Depending on the adaptation of the resistances to each other, in case of constant temperature and constant barometer level or with suitable temperature and absolute-pressure compensation the pressure drop measured on the difference-pressure measuring device 6 is proportional to the standard Wobbe Index (in case of predominant influence of the laminar resistance 4b) or proportional to the operating gross calorific or net calorific value (in case of predominant influence of the turbulence resistance 9). The first laminar resistor 4a in the flow path is partially surrounded by a thermostat 17.

Signals for operating Wobbe Indices or standard gross calorific or net calorific values presuppose other suitable compensations of the influences of absolute pressure and temperature.

Figure 6:
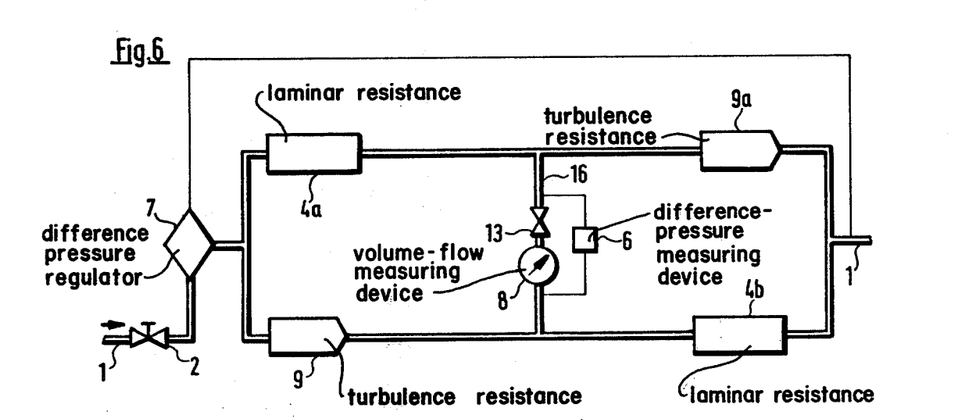
FIG. 6 is a schematic illustration of still another measuring arrangement of the present invention.

In the case of the measurement arrangement shown in FIG. 6, the gas line 1 is branched into two parallel line sections in each of which a laminar resistance 4 and a turbulence resistance 9 are arranged, a laminar resistance being present as a first resistance in the line section in one case and a turbulence resistance in the other case. The two line sections combine behind the measuring instruments again to form a common line and the difference-pressure regulator 7 maintains the pressure drop constant over the entire range of all flow resistances, as can be noted from the drawing. The measurement of a pressure drop or of a gas-volume flow takes place, in the case of this measurement arrangement, with the aid of corresponding devices 6 and 8 which are arranged in a bridge line 16 between the two parallel line sections—between the flow resistances—and can be acted upon alternately by means of the shut-off valve 13.

The advantage of this arrangement is that the indication is adjustable so that with a predetermined quality of gas a "null" signal is indicated. Upon change of the quality of gas it can be immediately noted from the signal whether a positive or a negative change has taken place. Furthermore, the signals deviating from the null position are relatively large, depending on the measuring instrument, at the start of the deviations since the curve of the deviations has an asymptotic course after an initial strong rise, particularly in the case of simple measuring instruments.

Figure 7:
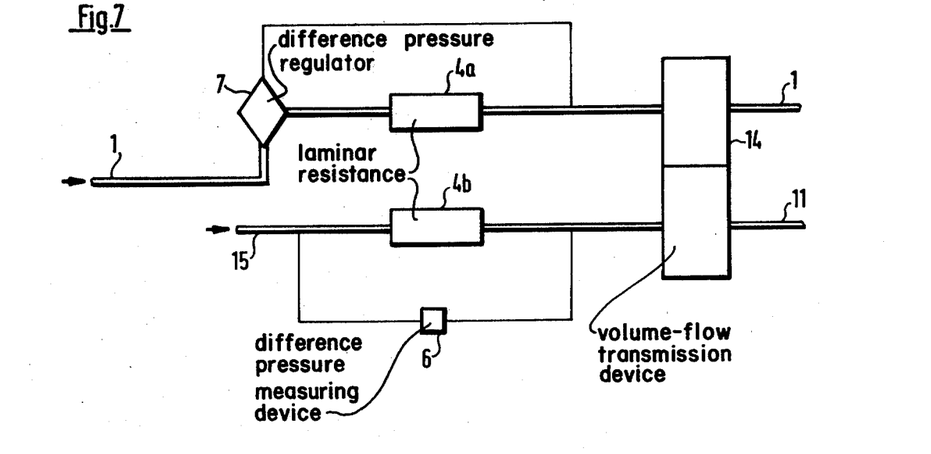
FIG. 7 is a schematic illustration of another measurement arrangment utilizing a second fluid line in accordance with the present invention.

By means of the measurement arrangement which is shown in FIG. 7, a measured fuel gas volume flow can be transferred to the volume flow of another fluid, preferably air, in the following manner: The fuel gas flows through a gas line 1 in which there is contained a laminar resistance 4a, the pressure drop of which is maintained constant by means of the difference pressure regulator 7, and thereupon through a volume-flow transmission device 14 which draws in, through line 15, a quantity of air corresponding to the quantity of fuel gas.

In the line 15, in front of the volume-flow transmission device 14 there is arranged a laminar resistance 4b whose pressure drop is measured by the difference-pressure measurement device 6. This measurement arrangement affords the advantage that the pressure drop measured at 6 is independent of the temperature and accordingly directly represents the signal for the standard Wobbe Index; in other words temperature compensation is unnecessary in the case of this measurement arrangement.

The laminar resistances consist suitably of one or more tubes of circular or annular cross section, particularly capillary tubes, whose ratio of length to hydraulic diameter is at least 20:1 and preferably 200 to 2000:1. The tubes are rounded at the inlet and conically expanded at the outlet. The angle between the cone and tube axis should be less than 20° and preferably less than 10°. Volume flows and cross sections of the tubes are so adapted to each other that the Reynolds number in no case exceeds a value of 2300. In this way the difference pressure produced between the inlet and end of the capillaries corresponds substantially to pure laminar flow.

The turbulence resistances comprise suitably thin orifice-diaphragms, the ratio of the orifice diameter to the length of which is greater than 2:1 and preferably is 5:1 to 20:1 and which are practically free of frictional resistances. In this way there is obtained, in front of and behind the diaphragm, a difference pressure which is produced practically only by the acceleration of the gas at the diaphragm and accordingly, even in the case of flows whose Reynolds number Re is less than 2300 therefore indicating laminar flow, still corresponds substantially to pure turbulent flow.

Figure 8:
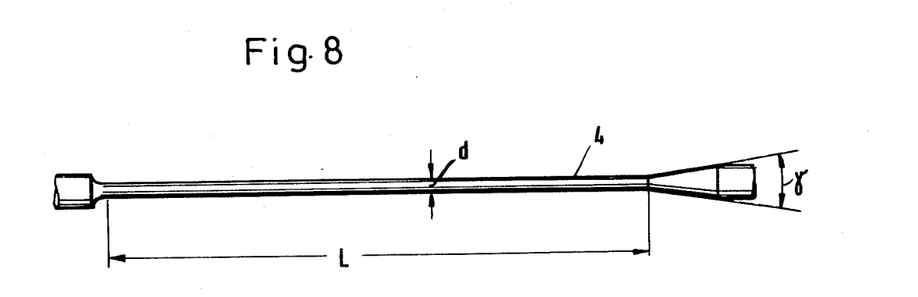
FIG. 8 shows a laminar resistor in elevational view partly broken away.
Figure 9:
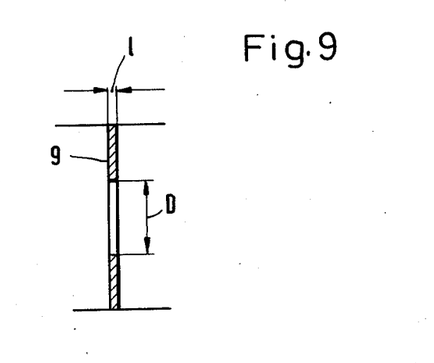
FIG. 9 shows a turbulence resistor in cross section formed as an orifice diaphragm.

FIG. 8 show a laminar resistor 4 of tubular shape with its length L to hydraulic diameter d being at least 20:1 and having a conical exit end. The conical angle $\gamma$ relative to the tube axis is smaller than 20 degrees. In FIG. 9 a turbulence resistor 9 comprises a perforated plate with its diameter of the hole D to the lengh 1 of the hole in the direction of the flow being greater than 2:1.

The temperature compensation can be effected, for instance, by thermostating at least one part of the first laminar resistance in the flow path or by changing the difference pressure of a difference pressure regulator.

If the temperature compensation is effected by a thermostating of a part of the first laminar resistance, it is advisable to use for this purpose the end of the resistance so that the rest of the resistance retains the surrounding temperature. Behind the resistance a heat exchanger sees to it that the remaining parts of the arrangement also retain the surrounding temperature.

In arrangements with a difference-pressure regulator on a flow resistance the temperature and absolute-pressure compensation can be effected in known manner by varying the load on the membrane of the pressure regulator.

If only one value is to be measured in the arrangements described above, this value can be used in known manner, directly or after conversion into other mechanical (for instance stroke) or electric signals, for instance in order to maintain the flow of energy constant for a gas-consumption device or for conversion of the gas-quantity indication of a gas meter into an energy-flow indication. If several values are to be measured, it is necessary to interpose a computer device which can combine several measured values to form one signal.

For the conversion of the volume-flow indication V of a gas meter into an energy flow Q, the relationship $$Q = H_o \cdot V \tag{17}$$

applies. The signal present from an arrangement for the determination of the gas gross calonific value displaces, for instance, on the gas meter, a gearing arranged in front of the display or acts on the stroke of the bellows in the gas meter so that $H_o \cdot V$ remains constant.

In order to maintain the heat load Q of a gas-consumption device constant, we have, with constant geometrical conditions, relationship (18) which can be derived from equations (1), (7) and (17) if the metering of the gas is effected via nozzles.

$$Q = k \cdot F \cdot \sqrt{\Delta p \cdot W_u} \tag{18}$$

If the Wobbe Index $W_u$ changes, then Q remains constant if $\sqrt{\Delta p} \cdot W_u$ is maintained constant by admixture of inert gases or gases of higher net calorific value $W_u$ or by action on the difference pressure $\Delta p$ at the gas nozzles, or if $F \cdot W_u$ is maintained constant by action on the free cross section F of the gas nozzle or on the cross section of an additional gas nozzle.

Literature References

[1] DIN 51950, Draft September 1978
[2] DIN 1871, February 1978
[3] D'Ans Lax, Taschenbuch für Chemiker und Physiker, 1967
[4] VDI-Wärmeatlas, 1974 Edition
[5] DVGW Guideline G 260, January 1973

TABLE 1

| COMPOSITION AND PROPERTIES OF NATURAL GASES WITHIN THE LIMITS OF G 260 | | | | | |
|---|---|---|---|---|---|
| | Unit | $H_{max.}$ | H | L | $L_{min.}$ |
| Gas analysis | | | | | |
| $CH_4$ | Vol. % | 83.2 | 92.9 | 81.8 | 77.3 |
| $C_2H_6$ | Vol. % | 10.0 | 3.0 | 2.8 | 2.8 |
| $C_2H_4^+$ | Vol. % | — | — | — | — |
| $C_3H_8$ | Vol. % | 4.3 | 1.5 | 0.4 | 0.3 |
| $C_4H_{10}$ | Vol. % | 1.0 | 0.4 | 0.1 | 0.1 |

TABLE 1-continued

COMPOSITION AND PROPERTIES OF NATURAL GASES WITHIN THE LIMITS OF G 260

| | Unit | $H_{max.}$ | H | L | $L_{min.}$ |
|---|---|---|---|---|---|
| $C_5^+$ | Vol. % | 0.2 | 0.2 | 0.1 | 0.1 |
| $H_2$ | Vol. % | — | — | — | — |
| CO | Vol. % | — | — | — | — |
| $CO_2$ | Vol. % | 1.0 | 1.0 | 1.0 | 1.0 |
| $N_2$ | Vol. % | 0.3 | 1.0 | 13.8 | 18.4 |
| $O_2$ | Vol. % | — | — | — | — |
| Gross calorific value $H_{o,n}$ | $MJ/m^3$ | 46.19 | 41.49 | 35.25 | 33.36 |
| Net calorific value $H_{u,n}$ | $MJ/m^3$ | 41.85 | 37.47 | 31.80 | 30.09 |
| Specific gravity (air = 1) $d_o$ | — | 0.678 | 0.609 | 0.643 | 0.661 |
| Viscosity/20° C. n . $10^5$ | $Ns/m^2$ | 10.46 | 10.83 | 11.96 | 12.32 |
| Viscosity/50° C. n . $10^6$ | $Ns/m^2$ | 11.39 | 11.78 | 12.97 | 13.35 |
| Upper Wobbe Index $W_{o,n}$ | $MJ/m^3$ | 56.10 | 53.17 | 43.96 | 41.03 |
| Lower Wobbe Index $W_{u,n}$ | $MJ/m^3$ | 50.83 | 48.01 | 39.66 | 37.01 |
| $W_u/W_{ub}$ | — | 1.059 | 1.000 | 0.826 | 0.771 |
| $H_o/H_{ob}$ | — | 1.113 | 1.000 | 0.850 | 0.804 |
| Upper Wobbe Index $W_{o,n}$ | kcal/$m^3$ | 13400 | 12700 | 10500 | 9800 |

We claim:

1. A process for the combustionless measurement and/or regulation of the feeding of quantities of heat to gas combustion devices, comprising the steps of conducting at least a partial stream of a fuel gas through at least one flow resistance which produces a laminar flow and a pressure drop, measuring at least one of the gas volume flow and the pressure drop over at least one flow resistance, maintaining constant at least one of the pressure drops and the gas volume flow which are not measured, compensating for the influence of temperature on the system, and deriving a signal for at least one of measurement and regulation utilizing the measured value(s) as a measure of the heat content of the flowing gas according to the formula:
$$f(H)=a+b \cdot n^c \cdot \rho^d$$

where:

f (H) being a function of heat of reaction of the gas;
a, b, c, and d are constants;
n is the dynamic gas viscosity which is obtained from the equation $n \sim (\Delta p_1/V_1)$
where $\Delta p_1$ is the pressure difference with laminar flow and $V_1$ is the volumetric flow; and
$\rho$ is the operating gas density which is obtained from the equation $\rho \sim (\Delta p_t/V_t^2)$ where $\Delta p_t$ and $V_t$ are the pressure difference and volumetric flow respectively with turbulent flow.

2. The method according to claim 1, wherein
said compensating for the influence of temperature comprises transmitting one of the measured gas volume flow and the pressure drop produced by a flow resistance in amount to an analogous measurement device which is traversed by another gas.

3. A method for the combustionless measurement and/or regulation of the quantity of heat fed to gas consumption devices, comprising the steps of conducting at least a partial stream of fuel gas through at least two flow resistances, at least one of which produces a laminar flow and another a turbulent flow and corresponding pressure drops, holding a constant pressure drop over at least one of said flow resistances, measuring the pressure drop over the other of said flow resistances, compensating for the influence of temperature, deriving a signal for at least one of measurement and regulation utilizing the measured value(s) as a measure of the heat content of the flowing gas according to the formula:

$$f(H)=a+b \cdot n^c \cdot \rho^d$$

where:

f (H) being a function of heat of reaction of the gas;
a, b, c, and d are constants;
n is the dynamic gas viscosity which is obtained from the equation $n \sim (\Delta p_1/V_1)$
where $\Delta p_1$ is the pressure difference with laminar flow and $V_1$ is the volumetric flow; and
$\rho$ is the operating gas density which is obtained from the equation $\rho \sim (\Delta p_t/V_t^2)$ where $\Delta p_t$ and $V_t$ are the pressure difference and volumetric flow respectively with turbulent flow.

4. A method for the combustionless measurement and/or regulation of the quantity of heat fed to gas consumption devices, comprising the steps of conducting at least a partial stream of fuel gas through at least two flow resistances, at least one of which produces a laminar flow and another a turbulent flow and corresponding pressure drops, maintaining a constant pressure drop over all of said flow resistances together, measuring the pressure drop over at least one flow resistance, compensating for the influence of temperature, deriving a signal for at least one of measurement and regulation utilizing the measured value(s) as a measure of the heat content of the flowing gas according to the formula:

$$f(H)=a+b \cdot n^c \cdot \rho^d$$

where:

f (H) being a function of heat of reaction of the gas;
a, b, c, and d are constants;
n is the dynamic gas viscosity which is obtained from the equation $n \sim (\Delta p_1/V_1)$
where $\Delta p_1$ is the pressure difference with laminar flow and $V_1$ is the volumetric flow; and
$\rho$ is the operating gas density which is obtained from the equation $\rho \sim (\Delta p_t/V_t^2)$ where $\Delta p_t$ and $V_t$ are the pressure difference and volumetric flow respectively with turbulent flow.

5. The method according to claim 4, comprising
conducting the stream of gas through two parallel groups, each of said groups being of two flow resistances connected in series, producing a laminar gas flow in one of the two flow resistances in each group and the turbulent gas flow in the other of said two flow resistances in each group, with the laminar gas flow being produced in a first of the two flow resistances in one of the groups and the laminar gas flow being produced in a last of the two flow resistances in the other group, the step of maintaining the pressure drop constant comprises maintaining the pressure drop over the two groups together constant, and the measuring step comprises measuring one of the pressure drop and the volume flow of the gas in a bridge between the two groups between the two flow resistances of each group.

6. The method according to claim 3 or 4, further comprising
conducting the fuel gas through and measuring the volume-flow of the fuel gas in a volume-flow measuring device.

7. The method according to claim 3 or 4, further comprising
conducting the fuel gas through and holding the volume-flow of the fuel gas constant by a volume-flow metering device.

8. The method according to claims 3 or 4, comprising the steps of
transmitting the measured pressure drops and volume flows to compensate for their influence to a microcomputer,
converting same in the microcomputer to one of a regulating pulse and control pulse.

9. The method according to claims 3 or 4, comprising the steps of
transmitting the measured pressure drops and volume flows to compensate for their influence to a microcomputer,
transmitting calculated values of same to at least one of display and recording instruments.

10. The method according to claims 1, 3, or 4, further comprising the step of
compensating for influence of absolute pressure.

11. The method according to claim 10, wherein
at least one of the steps of compensating for the influence of temperature and absolute pressure comprises acting on a membrane of a difference pressure regulator.

12. The method according to claim 1, 3, or 4, wherein
the step of compensating for the influence of temperature comprises thermostating a first laminar resistance in the flow path.

13. An arrangement for the combustionless measurement and/or regulation of the feeding of quantities of heat to gas combustion devices, comprising
means for conducting at least a partial stream of a fuel gas through at least one flow resistance which produces a laminar flow and a pressure drop,
means for measuring at least one of the gas volume flow and the pressure drop over at least one flow resistance,
means for maintaining constant at least one of the pressure drops and the gas volume flow which are not measured,
means for compensating for the influence of temperature on the system, and
means for deriving a signal for at least one of measurement and regulation utilizing the measured value(s) as a measure of the heat content of the flowing gas according to the formula: $f(H) = a + b \cdot n^c \cdot \rho^d$ where: $f(H)$ being a function of heat of reaction of the gas; a, b, c, and d are constants; n is the dynamic gas viscosity which is obtained from the equation $n \sim (\Delta p_1/V_1)$, where $\Delta p_1$ is the pressure difference with laminar flow and $V_1$ is the volumetric flow; and $\rho$ is the operating gas density which is obtained from the equation $\rho \sim (\Delta p_t/V_t^2)$, where $\Delta p_t$ and $V_t$ are the pressure difference and volumetric flow respectively with turbulent flow, and wherein
said conducting means is a fuel gas line,
said means for maintaining constant includes a volume flow-metering device, and
said at least one flow resistance includes at least one laminar resistor arranged in a flow path in the fuel gas line,
said measuring means comprises difference pressure measuring means operatively connected with said laminar resistor for the measuring of the pressure drop,
said means for compensating for the influence of temperature on the system includes a thermostat,
a first of said at least one laminar resistor in the flow path is partially surounded by said thermostat.

14. An arrangement for the combustionless measurement and/or regulation of the feeding of quantities of heat to gas combustion devices, comprising
means for conducting at least a partial stream of a fuel gas through at least one flow resistance which produces a laminar flow and a pressure drop,
means for measuring at least one of the gas volume flow and the pressure drop over at least one flow resistance,
means for maintaining constant at least one of the pressure drops and the gas volume flow which are not measured,
means for compensating for the influence of temperature on the system, and
means for deriving a signal for at least one of measurement and regulation utilizing the measured value(s) as a measure of the heat content of the flowing gas according to the formula: $f(H) = a + b \cdot n^c \cdot \rho^d$ where: $f(H)$ being a function of heat of reaction of the gas; a, b, c, and d are constants; n is the dynamic gas viscosity which is obtained from the equation $n \sim (\Delta p_1/V_1)$, where $\Delta p_1$ is the pressure difference with laminar flow and $V_1$ is the volumetric flow; and $\rho$ is the operating gas density which is obtained from the equation $\rho \sim (\Delta p_t/V_t^2)$, where $\Delta p_t$ and $V_t$ are the pressure difference and volumetric flow respectively with turbulent flow, and wherein
said conducting means is a fuel gas line,
said measuring means comprises a volume-flow measuring device,
said at least one flow resistance includes at least one laminar resistor and at least one difference pressure regulator means arranged in a flow path in said fuel gas line, said regulator means constitutes said means for maintaining constant and is for maintaining constant the pressure drop on said laminar resistor,
said means for compensating for the influence of temperature includes a thermostat,
a first of said at least one laminar resistor in the flow path is partially surrounded by said thermostat.

15. An arrangement for the combustionless measurement and/or regulation of the quantity of heat fed to gas consumption devices, comprising
means for conducting at least a partial stream of fuel gas through at least two flow resistances, at least one of which produces a laminar flow and another a turbulent flow and corresponding pressure drops,
means for holding a constant pressure drop over at least one of said flow resistances,
means for measuring the pressure drop over the other of said flow resistances, means for compensating for the influence of temperature, means for deriving a signal for at least one of measurement and regulation utilizing the measured value(s) as a measure of the heat content of the flowing gas according to the formula: $f(H)=a+b\cdot n^c\cdot\rho^d$ where: f(H) being a function of heat of reaction of the gas; a, b, c, and d are constants; n is the dynamic gas viscosity which is obtained from the equation $n\sim(\Delta p_1/V_1)$, where $\Delta p_1$ is the pressure difference with laminar flow and $V_1$ is the volumetric flow; and $\rho$ is the operating gas density which is obtained from the equation $\rho\sim(\Delta p_t/V_t^2)$, where $\Delta p_t$ and $V_t$ are the pressure difference and volumetric flow respectively with turbulent flow, and wherein said conducting means is a fuel gas line, said at least two flow resistances include at least one laminar flow resistor and one turbulence flow resistor arranged in said fuel gas line, said measuring means comprises a difference pressure measuring means connected with at least one of said flow resistors, said means for holding a constant pressure drop comprises a difference pressure regulator connected with the other said flow resistors.

16. The arrangement according to claim 15, further comprising a microcomputer, said difference pressure measurement means is connected with said microcomputer.

17. An arrangement for the combustionless measurement and/or regulation of the quantity of heat fed to gas consumption devices, comprising means for conducting at least a partial stream of fuel gas through at least two flow resistances, at least one of which produces a laminar flow and another a turbulent flow and corresponding pressure drops, means for holding a constant pressure drop over at least one of said flow resistances, means for measuring the pressure drop over at least one of said flow resistances, means for compensating for the influence of temperature, means for deriving a signal for at least one of measurement and regulation utilizing the measured value(s) as a measure of the heat content of the flowing gas according to the formula: $f(H)=a+b\cdot n^c\cdot\rho^d$ where: f (H) being a function of heat of reaction of the gas; a, b, c, and d are constants; n is the dynamic gas viscosity which is obtained from the equation $n\sim(\Delta p_1/V_1)$, where $\Delta p_1$ is the pressure difference with laminar flow and $V_1$ is the volumetric flow; and $\rho$ is the operating gas density which is obtained from the equation $\rho\sim(\Delta p_t/V_t^2)$, where $\Delta p_t$ and $V_t$ are the pressure difference and volumetric flow respectively with turbulent flow, and wherein said conducting means is a fuel gas line, said at least two flow resistances include at least one laminar flow resistor and one turbulence flow resistor being arranged in said fuel gas line, said means for holding a constant pressure drop comprises a difference pressure regulator means jointly connected with all said flow resistors, said measuring means comprises a difference pressure measuring means connected with at least one of said flow resistors.

18. The arrangement according to claim 15 or 17, further comprising a volume flow measuring device arranged in said fuel gas line.

19. The arrangement according to claim 18, further comprising a microcomputer, said volume-flow device is connected with said microcomputer.

20. The arrangement according to claim 15 or 17, further comprising a volume flow metering device arranged in said fuel gas line.

21. An arrangement for the combustionless measurement and/or regulation of the feeding of quantities of heat to gas combustion devices, comprising means for conducting at least a partial stream of a fuel gas through at least one flow resistance which produces a laminar flow and a pressure drop, means for measuring at least one of gas volume flow and the pressure drop over at least one flow resistance, means for maintaining constant at least one of the pressure drops and the gas volume flow which are not measured, means for compensating for the influence of temperature on the system, and means for deriving a signal for at least one of measurement and regulation utilizing the measured value(s) as a measure of the heat content of the flowing gas according to the formula: $f(H)=a+b\cdot n^c\cdot\rho^d$ where: f (H) being a function of heat of reaction of the gas; a, b, c, and d are constants; n is the dynamic gas viscosity which is obtained from the equation $n\sim(\Delta p_1/V_1)$, where $\Delta p_1$ is the pressure difference with laminar flow and $V_1$ is the volumetric flow; and $\rho$ is the operating gas density which is obtained from the equation $\rho\sim(\Delta p_t/V_t^2)$, where $\Delta p_t$ and $V_t$ are the pressure difference and volumetric flow respectively with turbulent flow, and wherein said conducting means is a fuel gas line and a reference gas line, said means for maintaining constant includes a difference pressure regulator, said at least one flow resistance includes a first laminar flow resistor, and a volume flow transmission device being arranged in said fuel gas line, said first laminar flow resistor being connected with said difference pressure regulator, a second laminar resistor disposed in said reference gas line, said volume flow transmission device is connected with said reference gas line, said measuring means comprises a difference pressure measurement means connected with said second laminar resistor for measuring the pressure drop across said second laminar resistor.

22. An arrangement for the combustionless measurement and/or regulation of the quantity of heat fed to gas consumption devices, comprising means for conducting at least a partial stream of fuel gas through at least two flow resistances, at least one of which produces a laminar flow and another a turbulent flow and corresponding pressure drops, means for holding a constant pressure drop over at least one of said flow resistances, means for measuring the pressure drop over the other of said flow resistances, means for compensating for the influence of temperature, means for deriving a signal for at least one of measurement and regulation utilizing the measured value(s) as a measure of the heat content of the flowing gas according to the formula: $f(H) = a30 \; b \cdot n^c \cdot \rho^d$ where: $f(H)$ being a function of heat of reaction of the gas; a, b, c, and d are constants; n is the dynamic gas viscosity which is obtained from the equation $n \sim (\Delta p_1/V_1)$, where $\Delta p_1$ is the pressure difference with laminar flow and $V_1$ is the volumetric flow; and $\rho$ is the operating gas density which is obtained from the equation $\rho \sim (\Delta p_t/V_t^2)$, where $\Delta p_t$ and $V_t$ are the pressure difference and volumetric flow respectively with turbulent flow, and wherein said conducting means is a fuel gas line, said at least two flow resistances include at least two laminar resistors and one turbulence resistor being arranged one behind the other in said fuel gas line, said means for holding a constant pressure drop comprises a difference pressure regulator, a volume flow metering device being connected with at least one of said laminar resistors, and with said difference pressure regulator, said volume flow metering device constitutes means for holding the volume flow in the fuel gas constant, said measuring means comprises a difference pressure measuring means connected with another of said laminar resistors and said turbulence resistor together.

23. An arrangement for the combustionless measurement and/or regulation of the quantity of heat fed to gas consumption devices, comprising means for conducting at least a partial stream of fuel gas through at least two flow resistances, at least one of which produces a laminar flow and another a turbulent flow and corresponding pressure drops, means for maintaining a constant pressure drop over all of said flow resistances together, means for measuring the pressure drop, means for compensating for the influence of temperature, means for deriving a signal for at least one of measurement and regulation utilizing the measured value(s) as a measure of the heat content of the flowing gas according to the formula: $f(H) = a + b \cdot n^c \cdot \rho^d$ where: $f(H)$ being a function of heat of reaction of the gas; a, b, c, and d are constants; n is the dynamic gas viscosity which is obtained from the equation $n \sim (\Delta p_1/V_1)$, where $\Delta p_1$ is the pressure difference with laminar flow and $V_1$ is the volumetric flow; and $\rho$ is the operating gas density which is obtained from the equation $\rho \sim (\Delta p_t/V_t^2)$, where $\Delta p_t$ and $V_t$ are the pressure difference and volumetric flow respectively with turbulent flow, and wherein said conducting means is a fuel gas line, a pressure reducer arranged in said fuel gas line, said fuel gas line divides between two division points into two parallel partial flow lines downstream of said pressure reducer, said at least two flow resistances include at least one laminar resistor and at least one turbulence resistor arranged on behind the other in each of said partial flow lines, said at least one laminar resistor in one of said partial flow lines is arranged in front of said at least one turbulence resistor in said one partial flow line, and said at least one laminar resistor in the other of said partial flow lines is arranged behind said at least one turbulence resistor in said other partial flow lines, said means for maintaining a constant pressure drop comprises a difference pressure regulator connected to said fuel gas line downstream of and upstream of said division points, respectively, a bridge line connects said two partial flow lines with each other between said at least one laminar resistor and at least one turbulence resistor in each of said partial flow lines, said measuring means comprises a difference pressure measurement device being operatively connected to said bridge line.

24. An arrangement for the combustionless measurement and/or regulation of the quantity of heat fed to gas consumption devices, comprising means for conducting at least a partial stream of fuel gas through at least two flow resistances, at least one of which produces a laminar flow and another a turbulent flow and corresponding pressure drops, means for maintaining a constant pressure drop over all of said flow resistances together, means for measuring the volume flow, means for compensating for the influence of temperature, means for deriving a signal for at least one of measurement and regulation utilizing the measured value(s) as a measure of the heat content of the flowing gas according to the formula: $f(H) = a + b \cdot n^c \cdot \rho^d$ where: $f(H)$ being a function of heat of reaction of the gas; a, b, c, and d are constants; n is the dynamic gas viscosity which is obtained from the equation $n \sim (\Delta p_1/V_1)$, where $\Delta p_1$ is the pressure difference with laminar flow and $V_1$ is the volumetric flow; and $\rho$ is the operating gas density which is obtained from the equation $\rho \sim (\Delta p_t/V_t^2)$, where $\Delta p_t$ and $V_t$ are the pressure difference and volumetric flow respectively with turbulent flow, and wherein said conducting means is a fuel gas line, a pressure reducer arranged in said fuel gas line, said fuel gas line divides between two division points into two parallel partial flow lines downstream of said pressure reducer, said at least two flow resistances include at least one laminar resistor and at least one turbulence resistor arranged one behind the other in each of said partial flow lines, said at least one laminar resistor in one of said partial flow lines is arranged in front of said at least one turbulence resistor in said one partial flow line, and said at least one laminar resistor in the other of said partial flow lines is arranged behind said at least one turbulence resistor, in said other partial flow lines, said means for maintaining a constant pressure drop comprises a difference pressure regulator connected to said fuel gas line downstream of and upstream of said division points, respectively, a bridge line connects said two partial flow lines with each other between said at least one laminar resistor and at least one turbulence resistor in each of said partial flow lines, said measuring means comprises a volume-flow measuring device being arranged in said bridge line.

25. The arrangement system according to claim 13, 14, 21, 23, or wherein
said laminar resistor is formed as at least one tube having a ratio of length to hydraulic diameter of at least 20:1,
each said at least one tube is rounded at an inlet and conically widened at an outlet thereof, the conical widening forming an angle relative to the axis of the tube of less than 20 degrees.

26. The arrangement according to claim 25, wherein said at least one tube has a circular cross-section.

27. The arrangement system acording to claim 25, wherein said at least one tube has an annular cross-section.

28. The arrangement system according to claim 25, wherein said ratio is 200 to 2000:1.

29. The arrangement according to claim 25, wherein said angle is less than 10 degrees.

30. The arrangement according to claims 23 or 24, wherein
said turbulence resistor is formed as an orifice diaphragm, the ratio of the diameter of the orifice to the length being greater than 2:1.

31. The arrangement according to claim 30, wherein said ratio is between 2:1 to 20:1.

32. The arrangement according to claims 23 or 24, further wherein
said compensating means includes a thermostat,
a first of said at least one laminar resistor in a flow path is at least partially surrounded by said thermostat.

33. The apparatus according to claims 14, 21, 23, or 24, wherein
said difference pressure regulator has a membrane which is acted on by a force which is dependent on at least one of temperature and absolute pressure.

34. An arrangement for the combustionless measurement and/or regulation of the quantity of heat fed to gas consumption devices, comprising
means for conducting at least a partial stream of fuel gas through at least two flow resistances, at least one of which produces a laminar flow and another a turbulent flow and corresponding pressure drops,
means for maintaining a constant pressure drop over all of said flow resistances together,
means for measuring the pressure drop over at least one flow resistance,
means for compensating for the influence of temperature,
means for deriving a signal for at least one of measurement and regulation utilizing the measured value(s) as a measure of the heat content of the flowing gas according to the formula: $f(H) = a + b \cdot n^c \cdot \rho^d$ where: f (H) being a function of heat of reaction of the gas; a, b, c, and d are constants; n is the dynamic gas viscosity which is obtained from the equation $n \sim (\Delta p_l / V_l)$, where $\Delta p_l$ is the pressure difference with laminar flow and $V_l$ is the volumetric flow; and $\rho$ is the operating gas density which is obtained from the equation $\rho \sim (\Delta p_t / V_t^2)$, where $\Delta p_t$ and $V_t$ are the pressure difference and volumetric flow respectively with turbulent flow, and wherein
said conducting means is a fuel gas line,
said at least two flow resistance include at least one laminar flow resistor and one turbulence flow resistor being arranged in said fuel gas line,
said means for maintaining a constant pressure drop comprises a difference pressure regulator means jointly connected with all said flow resistors,
said measuring means comprises a difference pressure measuring means connected with at least one of said flow resistors.

* * * * *